United States Patent
Chao

(10) Patent No.: US 8,842,270 B2
(45) Date of Patent: Sep. 23, 2014

(54) METHOD AND INSPECTION DEVICE FOR BRIGHT SPOT DEFECT DETECTION OF A POLARIZER

(75) Inventor: Shin-Min Chao, Taoyuan (TW)

(73) Assignee: BENQ Materials Corp., Taoyuan (TW)

( * ) Notice: Subject to any disclaimer, the term of this patent is extended or adjusted under 35 U.S.C. 154(b) by 325 days.

(21) Appl. No.: 13/214,134

(22) Filed: Aug. 19, 2011

(65) Prior Publication Data

US 2012/0212741 A1   Aug. 23, 2012

(30) Foreign Application Priority Data

Feb. 22, 2011   (TW) .............................. 100105777 A

(51) Int. Cl.
*G01N 21/00*   (2006.01)
*G01N 21/958*   (2006.01)

(52) U.S. Cl.
CPC .................................. *G01N 21/958* (2013.01)
USPC ................... 356/237.1; 356/237.2; 356/239.2

(58) Field of Classification Search
USPC ...................................................... 356/237.1
See application file for complete search history.

(56) References Cited

U.S. PATENT DOCUMENTS

| | | | |
|---|---|---|---|
| 4,028,728 A * | 6/1977 | Sharp ............................. | 348/131 |
| 2002/0159626 A1 * | 10/2002 | Shiomi et al. .................. | 382/145 |
| 2009/0141027 A1 * | 6/2009 | Sato et al. ...................... | 345/426 |
| 2010/0294418 A1 * | 11/2010 | Yura et al. ........................ | 156/64 |
| 2011/0274342 A1 * | 11/2011 | Maeda et al. ................... | 382/149 |

\* cited by examiner

*Primary Examiner* — Tarifur Chowdhury
*Assistant Examiner* — Hina F Ayub
(74) *Attorney, Agent, or Firm* — Ladas & Parry, LLP

(57) ABSTRACT

A method of bright spot defect detection for a polarizer is to be performed by an inspection device and includes the steps of: a) obtaining gray values for pixels of an image of a detected region, that contains a target spot, on the polarizer; b) obtaining a gray value variation score from the gray values obtained for the detected region, the gray value variation score being indicative of gray value variation among the pixels of the image of the detected region; and c) comparing the gray value variation score obtained for the detected region with a threshold value to obtain a comparison result, and determining whether the target spot is a bright spot according to the comparison result.

7 Claims, 5 Drawing Sheets

METHOD AND INSPECTION DEVICE FOR BRIGHT SPOT DEFECT DETECTION OF A POLARIZER

CROSS-REFERENCE TO RELATED APPLICATIONS

This application claims priority to Taiwanese Patent Application No. 100105777 filed on Feb. 22, 2011, the disclosure of which is incorporated herein by reference.

BACKGROUND OF THE INVENTION

1. Field of the Invention

The present invention relates to a method of automated optical inspection and an inspection device performing the same, more particularly to a method of bright spot defect detection for a polarizer and an inspection device performing the same.

2. Description of the Related Art

After a polarizer is manufactured, it is inspected using an automated optical inspection (AOI) system for detection of defects (e.g., bright spots). During the inspection, the AOI system captures an image of a target surface of the polarizer, analyzes the image thus captured using image processing techniques, and indicates any defect detected during the analysis for subsequent inspection by human inspectors.

However, the AOI system may be tricked by glares caused by a release film on the polarizer to indicate non-defective spots as being defective for subsequent human inspection, which renders the inspection process less efficient. Specifically, for each inspected pixel of the image captured by the AOI system, the AOI system is configured to determine if a brightness value of the pixel exceeds a threshold value, and to mark the corresponding spot on the polarizer for subsequent human inspection if affirmative. Accordingly, non-defective spots in regions of the target surface of the polarizer that correspond to extremely bright glares may thus have brightness values higher than the threshold value, and may thus be subjected to subsequent human inspection.

SUMMARY OF THE INVENTION

Therefore, an object of the present invention is to provide a method of bright spot detection for a polarizer.

In one aspect, a method of bright spot defect detection for a polarizer, according to the present invention, is to be performed by an inspection device and includes the steps of:

a) obtaining gray values for pixels of an image of a detected region, that contains a target spot, on the polarizer;

b) obtaining a gray value variation score from the gray values obtained for the detected region, the gray value variation score being indicative of gray value variation among the pixels of the image of the detected region; and c) comparing the gray value variation score obtained for the detected region with a threshold value to obtain a comparison result, and determining whether the target spot is a bright spot according to the comparison result.

Another object of the present invention is to provide a method of determining a threshold value for use during bright spot defect detection of a polarizer.

In another aspect, a method of determining a threshold value for use during bright spot defect detection of a polarizer that has a number of detected regions each containing a target spot, according to the present invention, is to be performed by an inspection device and includes the steps of:

i) for each of the detected regions of the polarizer,
obtaining gray values for pixels of an image of the detected region, and
obtaining a gray value variation score from the gray values obtained for the detected region, the gray value variation score being indicative of gray value variation among the pixels of the image of the detected region; and ii) determining the threshold value based upon the gray value variation scores obtained for the detected regions of the polarizer.

Yet another object of the present invention is to provide an inspection device for bright spot defect detection of a polarizer.

In a further aspect, an inspection device for bright spot defect detection of a polarizer, according to the present invention, includes:

a gray value calculation unit for obtaining gray values for pixels of an image of a detected region, that contains a target spot, on the polarizer;

a gray value variation score evaluation unit coupled to the gray value calculation unit for obtaining a gray value variation score from the gray values obtained by the gray value calculation unit, the gray value variation score being indicative of gray value variation among the pixels of the image of the detected region; and a comparison unit for comparing the gray value variation score obtained by the gray value variation score evaluation unit for the detected region with a threshold value to obtain a comparison result, and for determining whether the target spot is a bright spot according to the comparison result.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
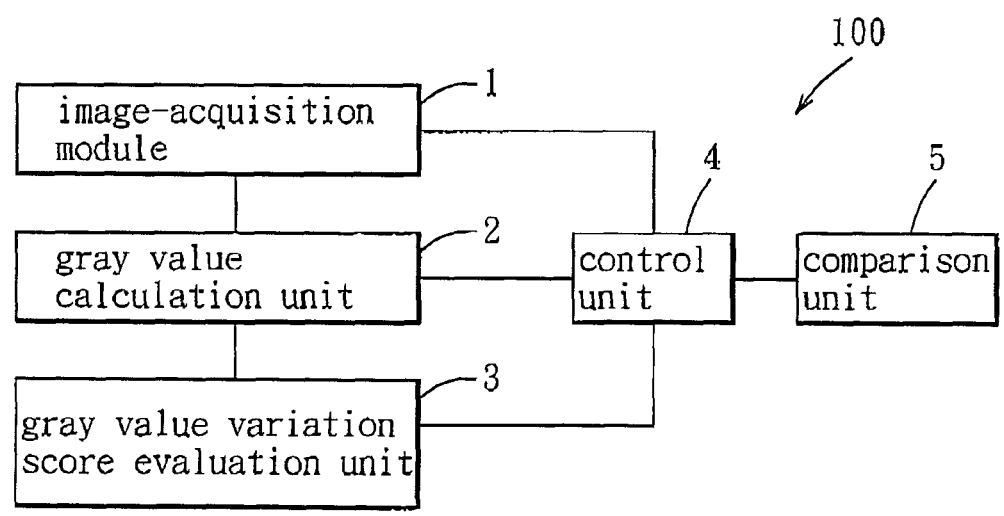
FIG. 1 is a block diagram to illustrate the preferred embodiment of an inspection device for bright spot defect detection of a polarizer, according to the present invention.

Before the present invention is described in greater detail, it should be noted that like elements are denoted by the same reference numerals throughout the disclosure.

Referring to FIG. 1, the preferred embodiment of an inspection device 100 of the present invention includes: an image acquisition module 1 (e.g., a camera); a gray value calculation unit 2 coupled to the image acquisition module 1; a gray value variation score evaluation unit 3 coupled to the gray value calculation unit 2; a control unit 4 coupled to the image acquisition module 1, the gray value calculation unit 2, and the gray value variation score evaluation unit 3; and a comparison unit 5 coupled to the control unit 4. The control unit 4 coordinates operations of the image acquisition module 1, the gray value calculation unit 2, the score generating unit 3, and the comparison unit 5.

Figure 2:
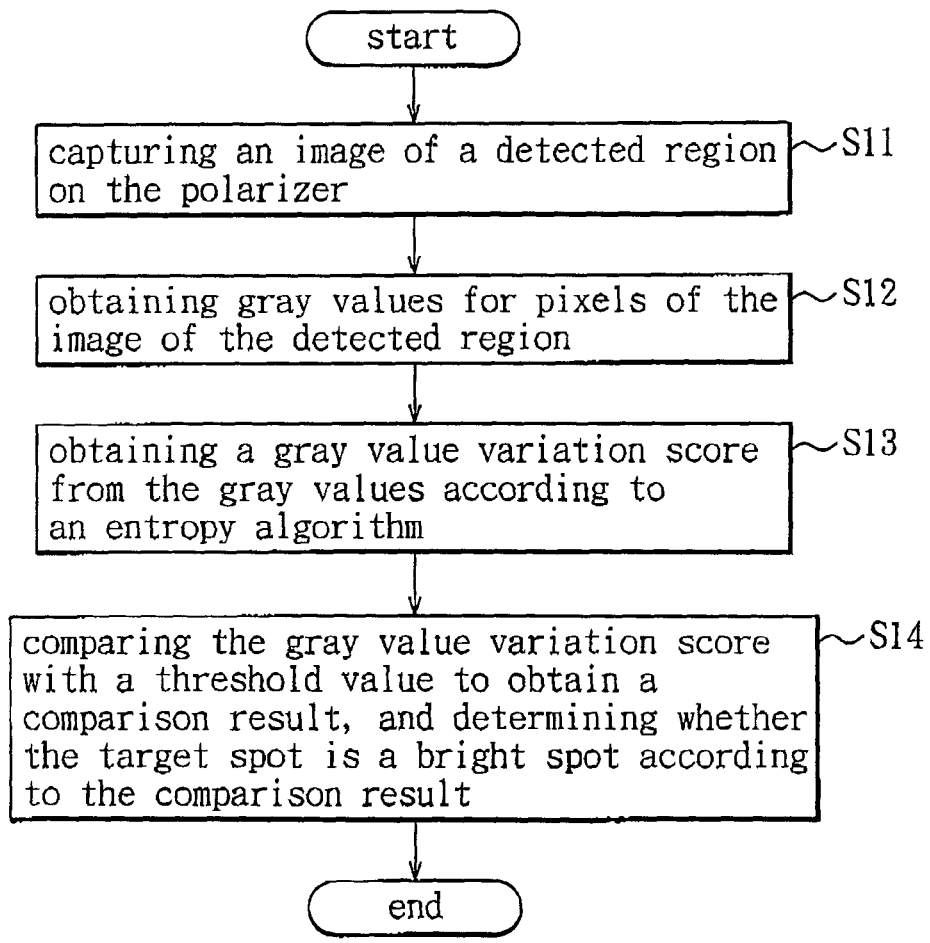
FIG. 2 is a flowchart to illustrate consecutive steps of the preferred embodiment of a method of bright spot defect detection for a polarizer, according to the present invention.

Referring to FIG. 2, the inspection device 100 is configured to perform the preferred embodiment of a method of bright spot defect detection for a polarizer.

Figure 3:
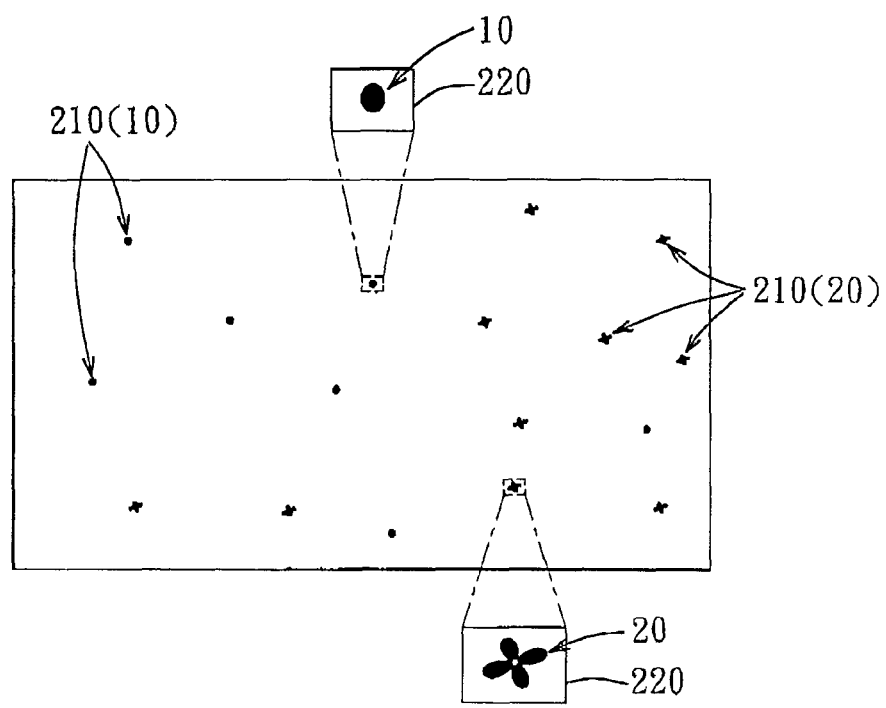
FIG. 3 is a schematic diagram to illustrate detected regions on a polarizer.

In step S11, the image acquisition module 1 is configured to capture an image of a detected region 220 on the polarizer (see FIG. 3). The detected region 220 contains a target spot 210 (e.g., a bright spot 10 or a glare spot 20). In this embodiment, the image thus captured has an image resolution of 200 pixels by 200 pixels (i.e., a square image having 40000 pixels). However, dimensions of the image are not limited to such, and may be adjusted according to need.

In step S12, the gray value calculation unit 2 is configured to obtain gray values for pixels of the image of the detected region 220. The gray value is indicative of gray value intensity of the corresponding pixel, and, in this embodiment, is an integer that falls within the range of 0 to 255.

In step S13, the gray value variation score evaluation unit 3 obtains a gray value variation score from the gray values that are obtained by the gray value calculation unit 2 according to an entropy algorithm. The entropy algorithm is defined as:

$$E = \sum_{i=0}^{L} p_i \times \ln(p_i)$$

where "L" is a predefined maximum gray value (i.e., 255), "i" is an integer index number, "$p_i$" is a ratio of the number of pixels having a gray value of "i" to the total number of pixels in the image (i.e., 40000), and "E" is the gray value variation score.

The gray value variation score thus acquired is indicative of complexity of the image. That is to say, the gray value variation score is a measure of variation in the gray values of the pixels of the image. A "$p_i$" value of one means that the image has a perfectly uniform distribution of gray values and a gray value variation score of zero. A "$p_i$" satisfying the condition of $p_i = p_j (\forall i \neq j)$ means that the image has at least two groups of pixels, each group having a unique gray value.

Figure 4A:
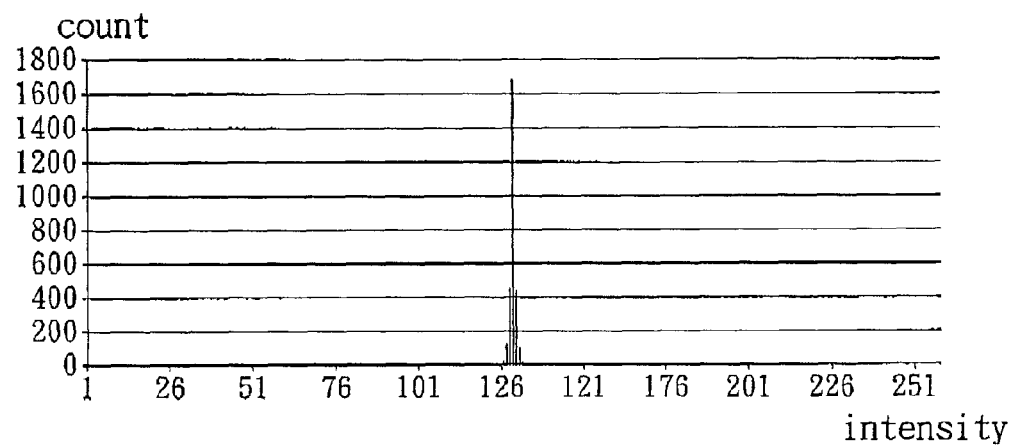
FIG. 4a is a diagram to illustrate distribution of gray values obtained for an image of a detected region that contains a bright spot.
Figure 4B:
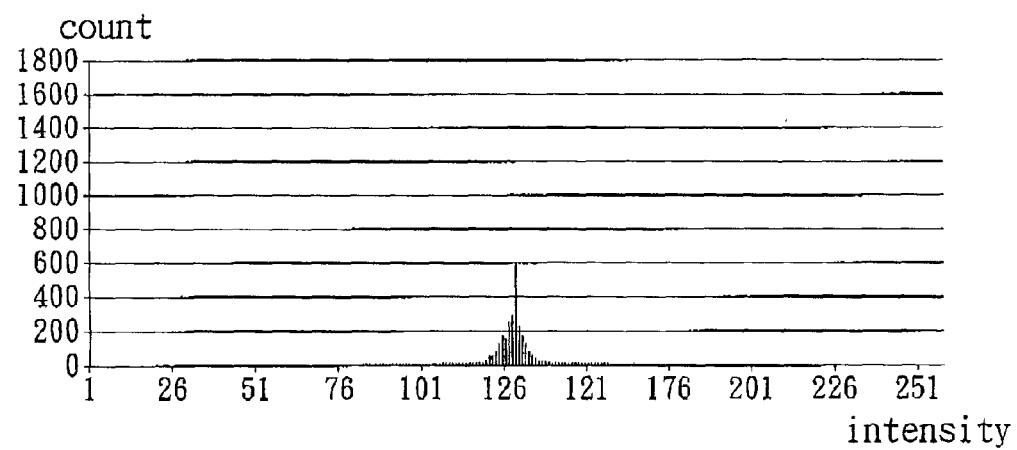
FIG. 4b is a diagram to illustrate distribution of gray values obtained for an image of a detected region that contains a glare spot.

FIG. 4a shows distribution of the gray values (i.e., gray value intensities) of an image of a detected region 220 that contains a bright spot 10. FIG. 4b shows distribution of the gray values of an image of a detected region 220 that contains a glare spot 20. It is apparent that the image corresponding to the bright spot 10 has a smaller range of variation in the gray values relative to the image corresponding to the glare spot 20. The image corresponding to the bright spot 10 thus has a lower score (i.e., lower complexity) relative to the image corresponding to the glare spot 20. It is worth noting that, in other embodiments, the gray value variation score may be obtained and presented otherwise. For example, the gray value variation score may be statistically obtained and presented by at least one of a variance value and a standard deviation value.

In step S14, the comparison unit 5 is configured to compare the gray value variation score obtained by the gray value variation score evaluation unit 3 with a threshold value to obtain a comparison result, and to determine whether the target spot is a bright spot according to the comparison result.

In this embodiment, the target spot is determined as being a bright spot 10 if the comparison result indicates that the gray value variation score is smaller than the threshold value, and is determined as being a glare spot 20 if the comparison result indicates that the gray value variation is not smaller than the threshold value. Target spots 210 that are indicated as being bright spots 10 may be subjected for subsequent human inspection.

Figure 5:
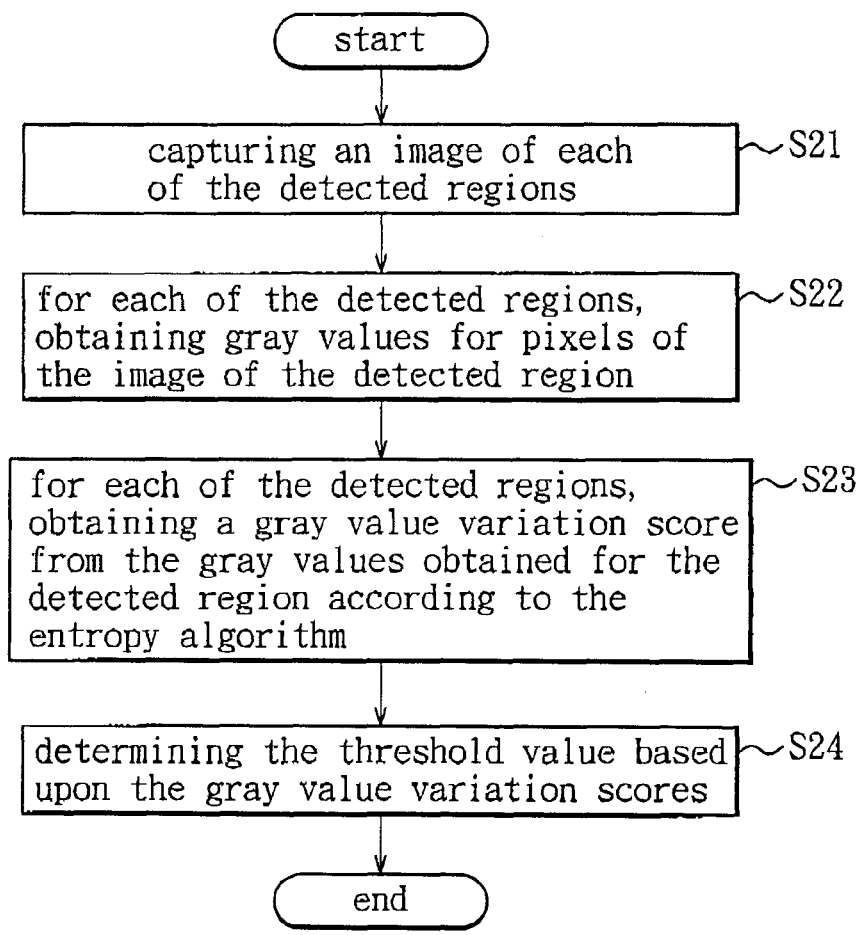
FIG. 5 is a flowchart to illustrate consecutive steps of the preferred embodiment of a method of determining a threshold value for use during bright spot defect detection of a polarizer, according to the present invention.

Referring to FIG. 5, prior to performing the aforesaid method of bright spot defect detection, the inspection device 100 may be configured to perform the preferred embodiment of a method of determining the threshold value for use during the subsequent bright spot defect detection of the polarizer, according to the present invention.

In step S21, the image acquisition module 11 is configured to capture an image of each of the detected regions 220.

In step S22, the gray value calculation unit 2 is configured to, for each of the detected regions 220, obtain gray values for pixels of the image of the detected region 220.

In step S23, the gray value variation score evaluation unit 3 is configured to, for each of the detected regions 220, obtain a gray value variation score from the gray values that are obtained by the gray value calculation unit 3 for the detected region 220 according to the entropy algorithm, the gray value variation score being indicative of gray value variation among the pixels of the image of the detected region 220.

In step S24, the comparison unit 5 is configured to determine the threshold value based upon the gray value variation scores obtained for the detected regions 220 in step S23.

Table 1 shows 59 entries of detected regions 220 and their corresponding gray value variation scores obtained using the present embodiment. The entries are arranged in a descending order of the scores.

TABLE 1

| Detected Region | Gray Value Variation Score |
|---|---|
| 1 | 0.3538 |
| 2 | 0.2116 |
| 3 | 0.2076 |
| 4 | 0.1793 |
| 5 | 0.1668 |
| 6 | 0.1656 |
| 7 | 0.1623 |
| 8 | 0.1599 |
| 9 | 0.1422 |
| 10 | 0.1315 |
| 11 | 0.1300 |
| 12 | 0.1300 |
| 13 | 0.1280 |
| 14 | 0.1260 |
| 15 | 0.1161 |
| 16 | 0.1115 |
| 17 | 0.1089 |
| 18 | 0.1056 |
| 19 | 0.1009 |
| 20 | 0.1002 |
| 21 | 0.0983 |
| 22 | 0.0969 |
| 23 | 0.0930 |
| 24 | 0.0861 |
| 25 | 0.0829 |
| 26 | 0.0689 |
| 27 | 0.0674 |
| 28 | 0.0442 |
| 29 | 0.0430 |
| 30 | 0.0371 |
| 31 | 0.0357 |
| 32 | 0.0331 |
| 33 | 0.0325 |

TABLE 1-continued

| Detected Region | Gray Value Variation Score |
|---|---|
| 34 | 0.0313 |
| 35 | 0.0313 |
| 36 | 0.0312 |
| 37 | 0.0304 |
| 38 | 0.0304 |
| 39 | 0.0294 |
| 40 | 0.0287 |
| 41 | 0.0283 |
| 42 | 0.0282 |
| 43 | 0.0282 |
| 44 | 0.0278 |
| 45 | 0.0276 |
| 46 | 0.0270 |
| 47 | 0.0261 |
| 48 | 0.0260 |
| 49 | 0.0259 |
| 50 | 0.0256 |
| 51 | 0.0251 |
| 52 | 0.0249 |
| 53 | 0.0246 |
| 54 | 0.0242 |
| 55 | 0.0241 |
| 56 | 0.0236 |
| 57 | 0.0230 |
| 58 | 0.0218 |
| 59 | 0.0217 |
| — | — |

In a combination of the aforesaid methods, the comparison unit 5 is configured to average the scores corresponding to target regions 27 and 28 so as to obtain the threshold value (0.0558), and to subsequently indicate the target spots 210 (i.e., the detected regions 220) that correspond to gray value variation scores lower than the threshold value thus obtained as being bright spots 10 for subsequent human inspection, and to indicate the target spots 210 that correspond to gray value variation scores not lower than the threshold value thus obtained as being glares spots 20. However, obtainment of the threshold value is not limited to such. For example, in another embodiment, an operator of the bright spot defect inspection device 100 may manually set the threshold value based on such as experience.

In summary, through performing the methods of the preferred embodiments, the inspection device 100 is able to obtain a relatively accurate result of bright spot defect detection, thereby improving efficiency of subsequent human inspection. The methods of the preferred embodiments may be embodied in a storage medium (e.g., an optical disc) in the form of a computer program product containing instructions that, when executed by a computing device (e.g., a computer), cause the computing device to perform steps of the aforesaid methods.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method of identifying whether a bright target spot on a polarizer is a bright spot defect or a glare spot, said method to be performed by an inspection device and comprising the steps of:

obtaining gray values for pixels of an image of a detected region of the polarizer, the detected region containing the bright spot target;

obtaining a gray value variation score from the gray values obtained for the detected region, the gray value variation score being indicative of gray value variation among the pixels of the image of the detected region;

comparing the gray value variation score obtained for the detected region with a threshold value to obtain a comparison result, and determining whether the target spot is a bright spot defect or a glare spot according to the comparison result; and subjecting the gray values to an entropy algorithm so as to obtain the gray value variation score, the entropy algorithm being defined as:

$$\sum_{i=0}^{L} p_i \times \ln(p_i)$$

where "L" is a predefined maximum gray value, "i" is an integer index number, "$p_i$" is a ratio of the number of pixels having a gray value of "i" to the total number of pixels in the image, and "E" is the gray value variation score.

2. The method as claimed in claim 1, wherein the bright target spot is determined as being a bright spot defect if the comparison result indicates that the gray value variation score is smaller than the threshold value.

3. The method as claimed in claim 1, wherein the gray value variation score obtained is represented by one of a variance value and a standard deviation value.

4. A computer program product containing instructions that, when executed by a computing device, cause the computing device to perform steps of a method of identifying whether a bright target spot on a polarizer is a bright spot defect or a glare spot as claimed in claim 1.

5. A method of determining a threshold value for use during identifying whether each of bright target spots on a polarizer is a bright spot defect or a glare spot, the polarizer having a number of detected regions, each containing a respective one of the bright target spots, said method to be performed by an inspection device and comprising the steps of:

for each of the detected regions of the polarizer:
    obtaining gray values for pixels of an image of a detected region, and
    obtaining a gray value variation score from the gray values obtained for the detected region, the gray value variation score being indicative of gray value variation among the pixels of the image of the detected region; and
determining the threshold value based upon the gray value variation scores obtained for the detected regions of the polarizer, wherein the gray values are subjected to an entropy algorithm so as to obtain the gray value variation score, the entropy algorithm being defined as:

$$\sum_{i=0}^{L} p_i \times \ln(p_i)$$

where "L" is a predefined maximum gray value, "i" is an integer index number, "$p_i$" is a ratio of the number of pixels having a gray value of "i" to the total number of pixels in the image, and "E" is the gray value variation score.

6. An inspection device for identifying whether a bright target spot on a polarizer is a bright spot defect or a glare spot, comprising:
   a gray value calculation unit for obtaining gray values for pixels of an image of a detected region, that contains the bright target spot, on the polarizer;
   a gray value variation score evaluation unit coupled to said gray value calculation unit for obtaining a gray value variation score from the gray values obtained by said gray value calculation unit, the gray value variation score being indicative of gray value variation among the pixels of the image of the detected region; and
   a comparison unit for comparing the gray value variation score obtained by said gray value variation score evaluation unit for the detected region with a threshold value to obtain a comparison result, and for determining whether the bright target spot is a bright spot defect or a glare spot according to the comparison result.

7. The inspection device as claimed in claim 6, further comprising an image acquisition module coupled to said gray value calculation unit and configured to capture the image of the detected region on the polarizer.

* * * * *